United States Patent [19]

Camaño

[11] Patent Number: 5,512,284
[45] Date of Patent: Apr. 30, 1996

[54] METHOD FOR TREATING BACTERIAL INFECTIONS

[75] Inventor: Ricardo M. Camaño, Montevideo, Uruguay

[73] Assignees: Teodoro P. Haidenvurcel; Eduardo H. Pinto, both of Montevideo, Uruguay

[21] Appl. No.: 75,117

[22] Filed: Jun. 10, 1993

[51] Int. Cl.$^6$ .......................... A61K 35/78; A61K 31/05; A61K 31/01; A61K 47/00
[52] U.S. Cl. ...................... 424/195.1; 424/405; 514/731; 514/762; 514/783
[58] Field of Search ...................... 514/731, 762, 514/783; 424/195.1, 405

[56] References Cited

U.S. PATENT DOCUMENTS 4,963,356  10/1990  Calenoff et al. .......................... 424/91
5,110,594  5/1992  Morita ...................................... 424/405

OTHER PUBLICATIONS

Chemical Abstracts 106(26) 219349m 1986.

A Handbook of Mexican Roadside Flora, Mason, Jr., et al., The University Of Arizona Press, 1987, pp. 52–57.

Primary Examiner—Raymond Henley, III
Assistant Examiner—Kevin E. Weddington

[57] ABSTRACT

The present invention relates to a SCHINUS MOLLE L. species essential oil composition with bactericide activity, being the components:

α PHELLANDRENE

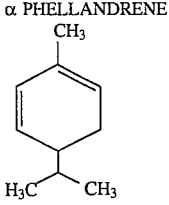

β PHELLANDRENE

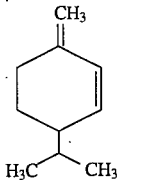

CARVACROL

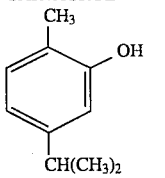

α PINENE

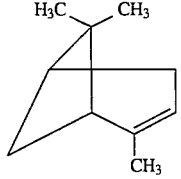

β PINENE
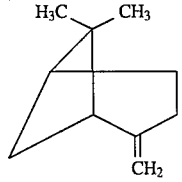

in an appropiate pharmaceutical dilution.

3 Claims, No Drawings

METHOD FOR TREATING BACTERIAL INFECTIONS

FIELD OF THE INVENTION

The present invention is related with an agent that contains essential oil bactericide activity of the *Schinus molle* L. species in an appropriate pharmaceutical dilution.

It arises from the microbiological analysis and the bactericide activity determination. The pharmacodynamics properties of this drug have a natural source and also have a topical application. Both characteristics are very important in those cases where resistance or intolerance to the systematic antimicrobial drugs exists.

In the present case, the pathogenic microorganisms, which are:

a) *Pseudomonas aeruginosa* and b) *Staphylococcus aureus* are killed by the drug, avoiding their development ability. Hence the fact that this drug has a principal roll in the wounds cleaning, reduction and elimination of the bacterial contamination.

A quick beginning of the bactericide action and a continuous activity are fundamental characteristics of the drug. Its liposolubility and capacity of dispersion are very important because they make the introduction into the protoplasm and microorganisms easier. These characteristics are very important when this drug is used in surgical wounded patients, avoiding or even eliminating the terrible postoperative shock by *Pseudomonas aeruginosa* fit which is not controlled in all the hospitals of the world.

The bactericide action depends on the following factors:

a) Concentration, b) Temperature and Ph, c) Vehicle of drug application and d) Time The time is an important factor, but is generally omitted or has not the appropriate pharmacokinetics importance, especially in those cases where time is a critical factor. According to Schmiedeberg, the pharmacodynamics actions should be the functional expression of the chemical nature reactions produced in the cellular plasms by influence of the administered medicines.

Nowadays, chemistry cannot explain all the phenomena of the medicinal action. The effects of these drugs should be explained by the presence of determinate atomic groups characterized in their molecule. For example, any substance that has the KETONEQUINONE—C6 02—group, that is to say aloes, rhubarb, cascara sagrada, etc, is laxative. It is certain that the pharmacodynamics action of the drug is not submitted to an only one physic and chemistry law.

The drug of the present invention was obtained from the distillation, at reduced pressure, of the leaves and soft branches of the *Schinus molle* L. species, of the Anacardiaceae family.

The present drug is an essential oil, obtained from the leaves and young branches of said plant. The essential oils are technically natural substances, very heterogeneous, which have vegetal sources and complex composition; and they are also one of the active properties of the plants.

According to the "World Health Organization" (WHO), a medicinal plant is "that one which contains active substances in one or more than one of their organs and that can be used with therapeutic purpose, or can be precursors of the chemistry-pharmaceutical semisynthesis process".

The word drug is used here from the point of view of Medical Botanical, pharmacognosy, as all vegetal source substance or a mixture of them, administered in its natural state or further manipulation with an exclusively therapeutical action purpose.

The *Schinus molle* L. species belongs to the botanical Anacardiaceae family (from the Greek ANA= above, CARDIA= core).

It is a resinous tree, which has a medium to high size, reaching 8–10 meters high in its adult age; and a thick trunk with hard and slightly furrowed bark, with a round somewhat foggy treetop, without thorns, large, with hanging branches of perennial, not dense and light green foliage.

It has glabrous, pinnatifid leaves of about 35 cm long, in 25–45 sessile folioles, dentate, complete or darkly spaced dentate, from 1 to 5 cm long and 2 to 5 mm wide, petiole from 2 to 4 cm, and slightly winged stalk.

The tree flowers are generally disposed in terminal bunches, from 10 to 20 long, in peduncles from 1,5 to 2 mm, calyx of 1 mm, glabrous, corolla with oblong petals longer than the calyx.

Its fruit is globe-shaped of about 4–5 mm of diameter and with a reddish epicarp.

In regard to the phytogeographical situation, the *Schinus molle* L. belongs to the botanical Uruguayan zone that comprises the territories of Uruguay, Mesopotamia and the west of Argentina, Paraguay and Bolivia.

It is usually found in Peru, Central America and in North America, specially in the State of California, where it grows well and it is planted because of its elegant and beautiful appearance.

The method used for its essential oil (drug) extraction, allows the isolation with a good yield, working with large quantities of material, and carrying out a steam distillation at reduced pressure, where the steam is produced in other vessel or boiler. In case that the process should be hastened it is convenient to combine the wet steam with dry steam to make the hydrodiffusion easier.

In the industry the stills that can be used are SCHIMMEL, OTTO, DEROY, or EGROT.

It is possible that aromatic distilled waters of the *Schinus molle* L. as an industrial subproduct, have an active participation in the fields of the medical cosmetology, pharmacy, drug trade, and aerosoles manufacture.

The dosis of drug, which has bactericide activity in vitro against *Pseudomonas aeruginosa* and *Staphylococcus aureus* strains (according to the microbiology analysis of the Beltrán-Zunino Laboratory, Montevideo), was prepared using alcohol at 95° C. as vehicle, according to:

Essential oil of *Schinus molle* L. (drug) 1 gr.

Alcohol at 95° C. (vehicle) 100 cc.

It is necessary to clarify that the above mentioned bactericide action is not due to the influence of the alcohol as vehicle; but according to the pharmacological kinetic and the chart of clinical status, all the vehicles, which are compatible with the pharmacognosy, pharmacodynamics, physiological, chemistry and dynamometric techniques principles, can be used in the formula.

Examples, the difference whereon the *Pseudomonas aeruginosa* is found in the ear and in surgical wounds. In regard to the factors that determine the susceptibility and the resistance of the microorganisms, the positive therapeutical result is the one whereon the drug dosis is enough to eradicate the microorganisms without causing toxicity in human cells. There were no signs of toxicity in the tests that were carried out and because of this the over-kill scope of the drug is quite extensive.

The identified components of the *Schinus molle* L. essential oil are:

*PHELLANDRENE

α Phellandrene    β Phellandrene

*ALDEHYDES AND KETONES
*CARVACROL

*PINENE

α Pinene    β Pinene

Other details:

extraction yield: about 3.05% organoleptic characteristics: a clear yellow liquid with pleasant smell.

specific weight at 20°: 0.9037 refractive index: 1.4921 polarimetric deviation: 2.80 ester number: 14.0 additional applications: the drug is useful against cutaneous infection in sheep by *Pseudomonas aeruginosa*, since the propagation of the bacterium towards the fleece affects its quality, because it gets a lemon yellow color, and determines the wool that must be discarded, producing an important decrease in the wool world market.

It is also useful against puerperal pathologies like Septic Metritis because of primary and/or secondary reasons in bovine cattle, swine and herd of breeding mares that is caused by *Pseudomonas aeruginosa*, producing serious repercussions over the female fertility. Other human therapeutic application is noticed when the present drug is provided in fluid extract form, the menstruation is regularized and/or the menopausic pathology is lightened in the case of amenorrhea and/or other irregularity conditions in the menstrual cycle.

The patient has shown *Pseudomonas aeruginosa* culture development in the left ear for about a two year-term. During this time, she was treated with antibiotics sensitive to the microorganism, but the results were negative.

At that step, the doctor used the usual topical application of acetic acid drops, diluted at 1% in alcohol vehicle at 95° C., with also negative results. In that situation, two drops of the dilution of the present drug in the said ear was provided with the aforesaid formulation, three times a day for three days, with positive results, disappearing the *Pseudomonas aeruginosa* without causing toxicity in the human cells.

The drug is at present used with glicerine USP as vehicle for the eradication of *Staphylococcus aureus* cultures in nose and throat. According to the exudate, a decrease of said microorganism concentration is noticed in a three day-term. The drug concentration can be increased or the therapeutical application time can be prolonged, because the over-kill time is very long.

BACTERICIDE ACTIVITY DETERMINATION

Beltran-Zunino Laboratory

Assay

Strains:
 1. *Staphylococcus aureus* ATCC 29737
 2. *Pseudomonas aeruginosa* ATCC 29366

Product concentration: 100%

Exposition time: 10 minutes

Results

Original bacterial concentration:
 1. $1.1 \times 10^6$ ufc/ml
 2. $1.0 \times 10^6$ ufc/ml Final bacterial concentration:
 1. <1 ufc/ml
 2. <1 ufc/ml Conclusion:

Efficiency:
 1. >99.9999%
 2. >99.9999%

According to the pharmacological kinetic, the present drug at 1.5% dilution with glicerine in pharmaceutical degree USP as vehicle was provided over the following chart of clinical status:

a) Local symptoms: Presence of open, bleeding wounds with big suppuration in the external backpart of the right leg. A greenish yellow purulent running sore with fetid smell, small and medium vesicles with aqueous content of amberlike color, swelling, inflammation and color in the zone were noticed for five months.

b) General symptoms: High temperature, about 38.5° C., depression, light anorexy.

According to the bacteriological exudate, a great number of *Pseudomonas aeruginosa* colonies were noticed. According to the antibiogram, Lazar Ciprofloxacine was prescribed and provided via oral, but improvement in health was not noticed.

According to the detailed kinetic, when the present drug was provided in a topical form once a day, for ten days, an improvement in health was noticed on the second day. The temperature turns to normal temperature and the suppuration stops. A reepithelization in the zone was observed on the fifth day.

ANALYSIS OF THE LEG ULCER EXUDATE

Spanish Association

Epithelial cells, small quantity of polynuclear cells and abundant quantity of negative-Gram bacillus were observed.

| Culture: | |
|---|---|
| Development of abundant *Pseudomonas aeruginosa* colonies. | |
| Antibiogram: | |
| First line Gentamicin | sensitive |

-continued

| | |
|---|---|
| Second line | intermediate |
| Cefoperazone | |
| External use | |
| Neomicin | sensitive |
| Kanamicin | strong |
| Polymyxin B | sensitive |

I claim:

1. A method for treating infections of *Pseudomonas aeruginosa* and *Staphylococcus aureus* in a human or animal patient, comprising applying a pharmaceutical composition to the patient's epidermis, wherein said pharmaceutical composition comprises an essential oil extract from *Schinus molle L.* and a pharmaceutically acceptable carrier and wherein said essential oil extract further comprises α-phellandrene, β-phellandrene, carvacrol, α-pinene and β-pinene in a clear yellow liquid with specific weight at 2° C. of about 0.9, a refractive index of about 1.49, a polarimetric deviation of about 2.8, an ester number of about 14.

2. The method of claim 1 wherein the pharmaceutical composition is applied to the patient's ear, nose, or throat.

3. The method of claim 1 wherein the pharmaceutical composition is applied to an infected site or a surgical incision.

* * * * *